United States Patent
Camp et al.

(10) Patent No.: US 11,191,629 B2
(45) Date of Patent: Dec. 7, 2021

(54) MEDICAL DEVICE PACKAGING SYSTEM AND METHOD OF OPENING THE SAME

(71) Applicant: Merit Medical Systems, Inc., South Jordan, UT (US)

(72) Inventors: Harper Camp, North Salt Lake, UT (US); Christopher Cindrich, Highland, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 196 days.

(21) Appl. No.: 16/163,298

(22) Filed: Oct. 17, 2018

(65) Prior Publication Data

US 2019/0110879 A1 Apr. 18, 2019

Related U.S. Application Data

(60) Provisional application No. 62/573,794, filed on Oct. 18, 2017.

(51) Int. Cl.
| | |
|---|---|
| *A61F 2/00* | (2006.01) |
| *B65D 25/10* | (2006.01) |
| *B65D 5/72* | (2006.01) |
| *A61M 25/00* | (2006.01) |
| *B65D 21/08* | (2006.01) |
| *A61B 50/30* | (2016.01) |
| *A61F 2/95* | (2013.01) |

(52) U.S. Cl.
CPC ......... *A61F 2/0095* (2013.01); *A61M 25/002* (2013.01); *B65D 5/721* (2013.01);
(Continued)

(58) Field of Classification Search
CPC ............ A61F 2/0095; A61F 2250/0065; A61F 5520/0071; A61F 2250/0069; B65D 5/721; B65D 25/10; A61M 25/002
(Continued)

(56) References Cited

U.S. PATENT DOCUMENTS

| 2,353,761 A | * | 7/1944 | Ringler | ................ B65D 5/0005 |
| | | | | 229/101 |
| 3,363,821 A | * | 1/1968 | Melconian | ......... B65D 85/1027 |
| | | | | 206/267 |

(Continued)

FOREIGN PATENT DOCUMENTS

| EP | 3042857 | 7/2016 |
| FR | 2876086 | 10/2004 |

OTHER PUBLICATIONS

International Search Report and Written Opinion dated Jan. 31, 2019 for PCT/US2018/056335.
European Search Report dated Jul. 19, 2021 for EP18868505.1.

*Primary Examiner* — J. Gregory Pickett
*Assistant Examiner* — Jenine Pagan
(74) *Attorney, Agent, or Firm* — Stoel Rives LLP

(57) ABSTRACT

A medical device packaging system that includes a medical device packaged within an outer sleeve with an open end and a closure flap for closing an end opposite the open end. The packaging system further includes a seal that couples the closure flap to the outer sleeve to close the end opposite the open end. The seal is frangible along an edge between the closure flap and outer sleeve. The packaging system further includes an inner sleeve with a corresponding shape to the outer sleeve, and the outer sleeve and the inner sleeve are configured to move relative to each other in a longitudinal direction of the sleeves. The packaging system further includes a stiffener with a leading edge disposed within the inner and outer sleeves such that the leading edge of the stiffener is configured to interact with an inner surface of the closure flap.

8 Claims, 9 Drawing Sheets

(52) U.S. Cl.
CPC .......... *B65D 21/086* (2013.01); *B65D 25/10* (2013.01); *A61B 50/30* (2016.02); *A61B 2050/3006* (2016.02); *A61F 2/95* (2013.01); *A61F 2250/0065* (2013.01); *A61F 2250/0069* (2013.01); *A61F 2250/0071* (2013.01)

(58) Field of Classification Search
USPC .... 206/363, 807, 274, 270, 364; 220/8, 214, 220/DIG. 3; 229/125.125, 101
See application file for complete search history.

(56) References Cited

U.S. PATENT DOCUMENTS

| | | | | |
|---|---|---|---|---|
| 3,773,245 | A * | 11/1973 | Meyers | B65D 5/0218 229/129 |
| 4,392,605 | A * | 7/1983 | Backman | B65D 5/4279 206/1.5 |
| 6,499,241 | B1 * | 12/2002 | Vila-Martinez | B65D 55/06 206/807 |
| 7,604,117 | B2 | 10/2009 | Bourgoin et al. | |
| 7,673,748 | B2 * | 3/2010 | Norell | B65D 85/1054 206/443 |
| 8,701,889 | B2 * | 4/2014 | Loftin | B65D 77/006 206/528 |
| 2005/0045503 | A1 * | 3/2005 | Wong | B65D 55/06 206/308.2 |
| 2006/0124493 | A1 | 6/2006 | Krackow | |
| 2009/0288371 | A1 | 11/2009 | Squarzoni et al. | |
| 2011/0062175 | A1 | 3/2011 | Nakamura et al. | |
| 2012/0048751 | A1 | 3/2012 | Stopek et al. | |

\* cited by examiner

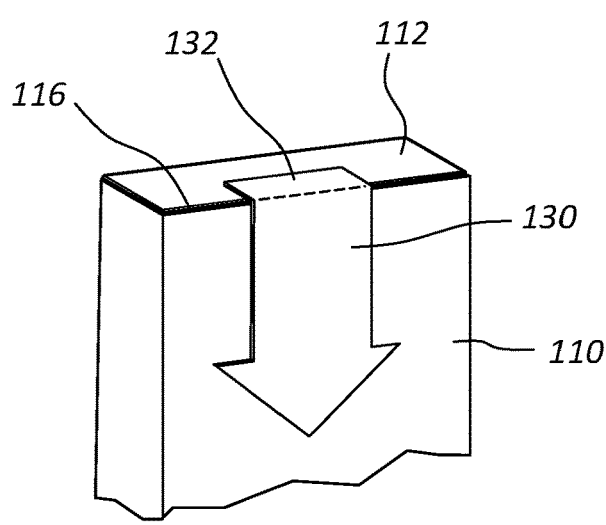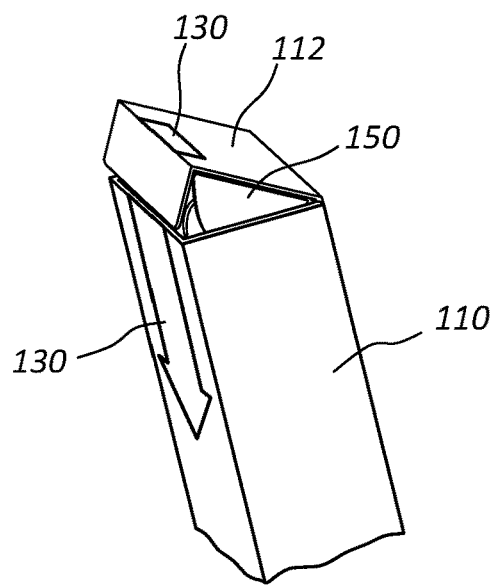
FIG. 6
FIG. 7
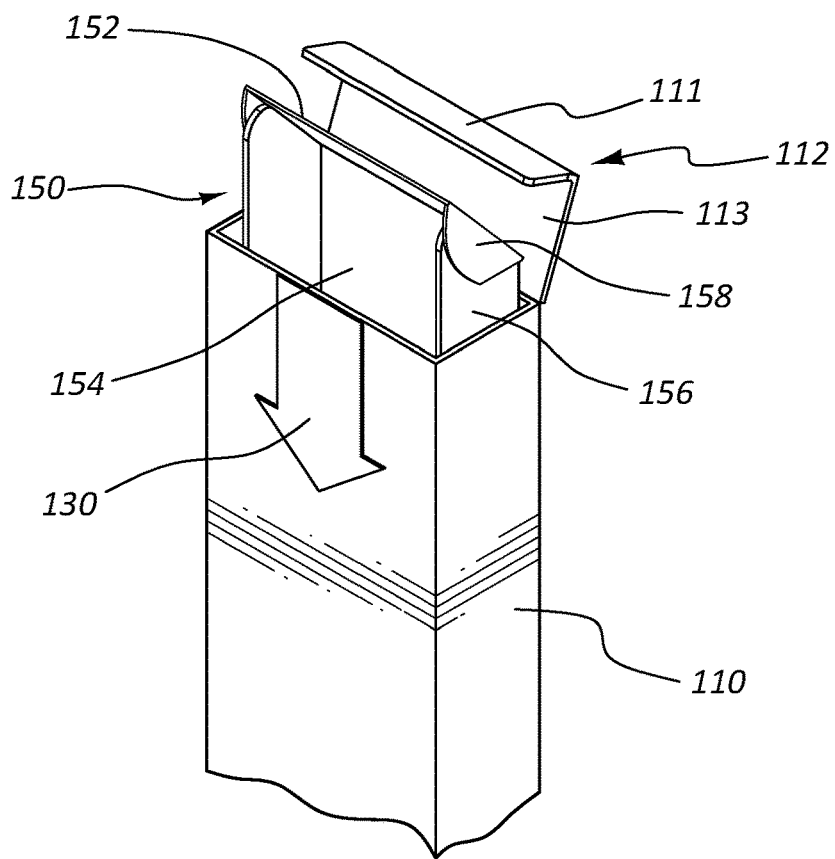
FIG. 8

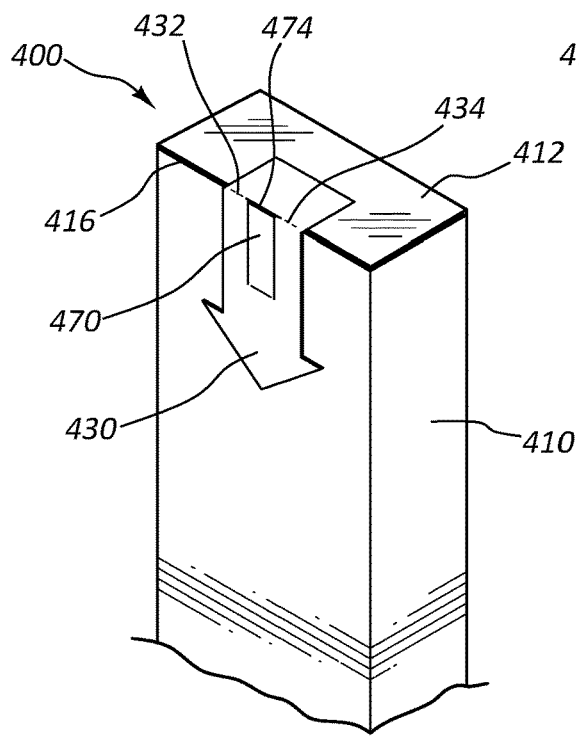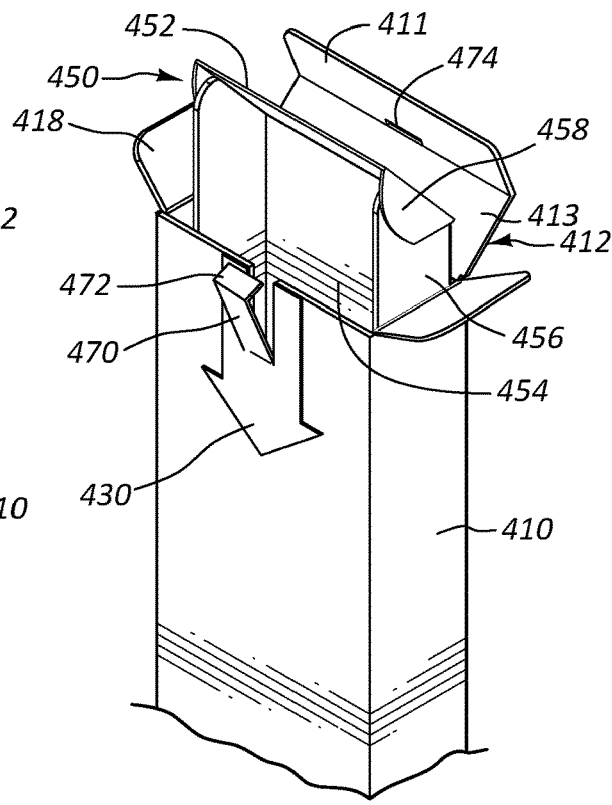
FIG. 14   FIG. 15
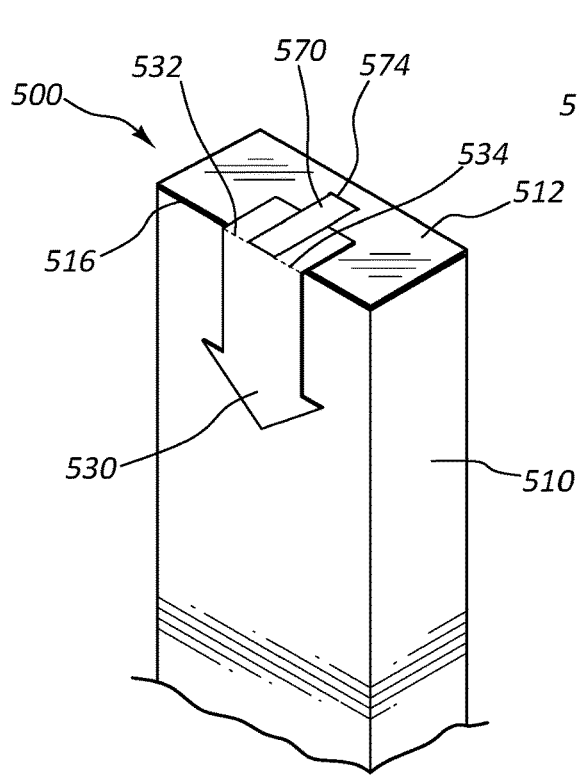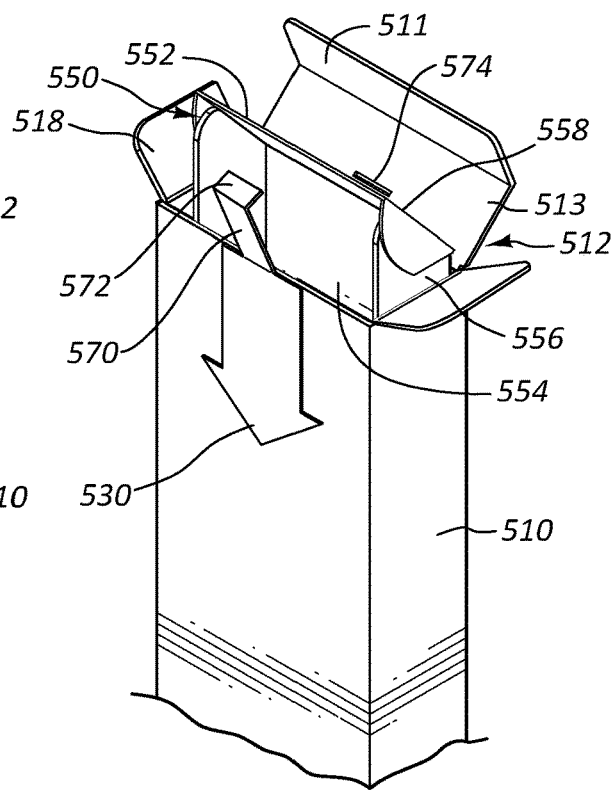
FIG. 16   FIG. 17

MEDICAL DEVICE PACKAGING SYSTEM AND METHOD OF OPENING THE SAME

RELATED APPLICATIONS

This application claims priority to U.S. Provisional Application No. 62/573,794, filed on Oct. 18, 2017 and titled, "Medical Device Packaging System and Method of Opening the Same," which is hereby incorporated by reference in its entirety.

TECHNICAL FIELD

The present disclosure relates generally to the field of medical devices. More particularly, some embodiments relate to packaging systems for medical devices and methods of opening the packaging systems.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 6 depicts a detailed view of an outer sleeve of the packaging system of FIG. 1 in a closed configuration.

FIG. 7 depicts a detailed view of the outer sleeve of the packaging system of FIG. 1 in a partially open configuration.

FIG. 8 depicts a detailed view of outer sleeve of the packaging system of FIG. 1 in an open configuration.

FIG. 14 depicts a detailed view of an embodiment of a packaging system for a medical device in a closed configuration.

FIG. 15 depicts a detailed view of the packaging system of FIG. 14 in an open configuration.

FIG. 16 depicts a detailed view of an embodiment of a packaging system for a medical device in a closed configuration.

FIG. 17 depicts a detailed view of the packaging system of FIG. 16 in an open configuration.

DETAILED DESCRIPTION

Figure 1:
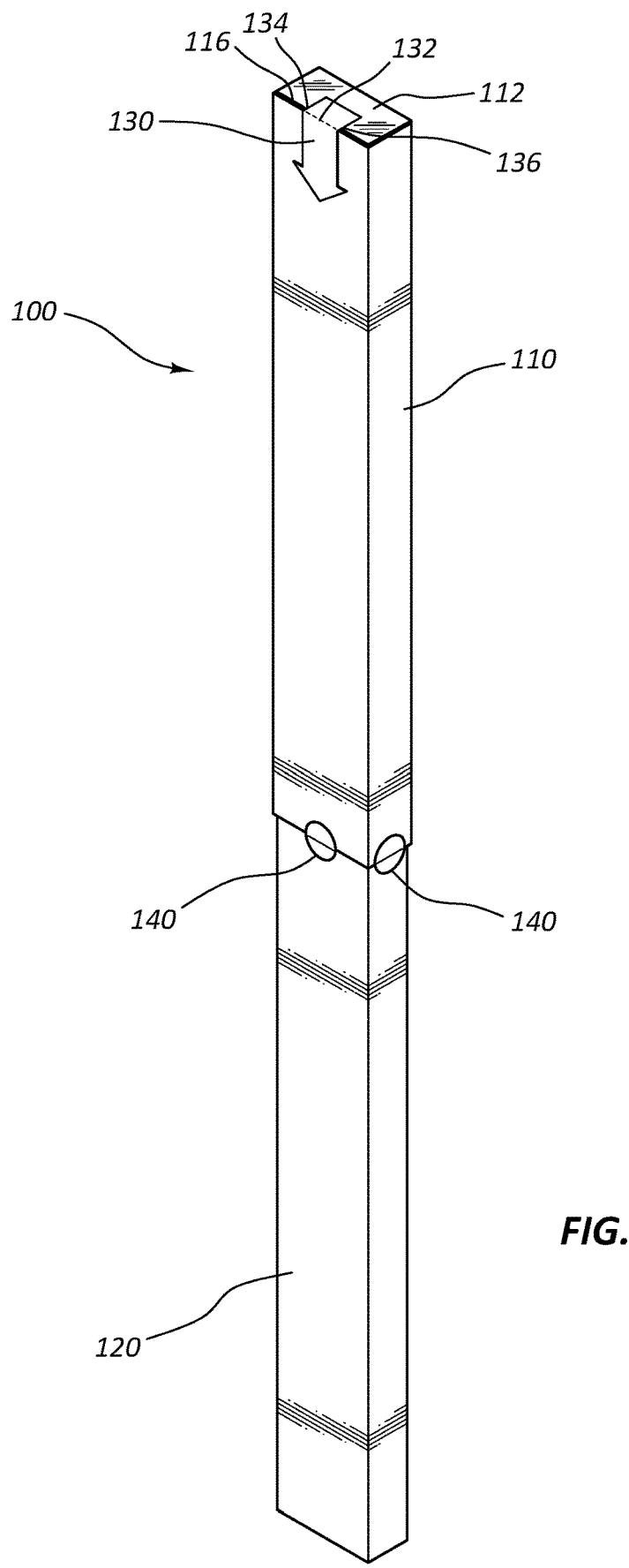
FIG. 1 is a perspective view of an embodiment of a packaging system for a medical device in a closed configuration.

Medical devices may be manufactured, sterilized, and packaged before being transported to medical facilities, hospitals, doctor offices, etc. One of the purposes of the packaging is to protect the medical device and maintain the sterility of the medical device during transportation of the medical device from the manufacturing facility to the final medical facility where the medical device will be used. The packaging of the medical device may be designed in such a way as to facilitate easy access to the medical device in the package (e.g., the method of opening the packaging). Easy access may enable medical professionals to access the medical device within the packaging without compromising the sterility of the medical device.

Medical devices come in all shapes and sizes. Some medical devices may be long or oddly shaped, making it difficult to package them in traditional boxes. Telescoping boxes enable a manufacturer to package long and/or oddly shaped devices in a package that may conform to the device's dimensions. Telescoping boxes may comprise two boxes, an inner box and an outer box, that slide relative to each other and enable a user to modify the overall length of the package. A medical device may be placed within the inner box and the outer box may be placed over the inner box. The inner box and the outer box may be adjusted to the medical device's specific dimensions and coupled together to fix the overall length of the package. Accordingly, since telescoping boxes are adjustable to the product being packaged, telescoping boxes can reduce the number of different size boxes a manufacturer keeps.

The design of the package of the medical device may help a medical professional easily access the medical device within the package. Due to constraints of operating rooms, etc., long and oddly shaped packages may be difficult to access in confined spaces. In addition, if a sharp instrument (e.g., scalpel, blade, razor, etc.) is needed to open the package, there is a possibility that the sharp instrument may cut the person opening the package, the person may damage the medical device within the package, or the person may compromise the sterility of the medical device. Accordingly, there is a need for packaging systems that can protect long and oddly shaped medical devices that are easy to open.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrase "coupled to" is broad enough to refer to any suitable coupling or other form of interaction between two or more entities. Thus, two components may be coupled to each other even though they are not in direct contact with each other. For example, two components may be coupled to each other through an intermediate component. The phrase "attached to" refers to interaction between two or more entities which are in direct contact with each other and/or are separated from each other only by a fastener of any suitable variety (e.g., an adhesive). Unless otherwise stated, all ranges include both endpoints and all numbers between the endpoints.

Figure 2:
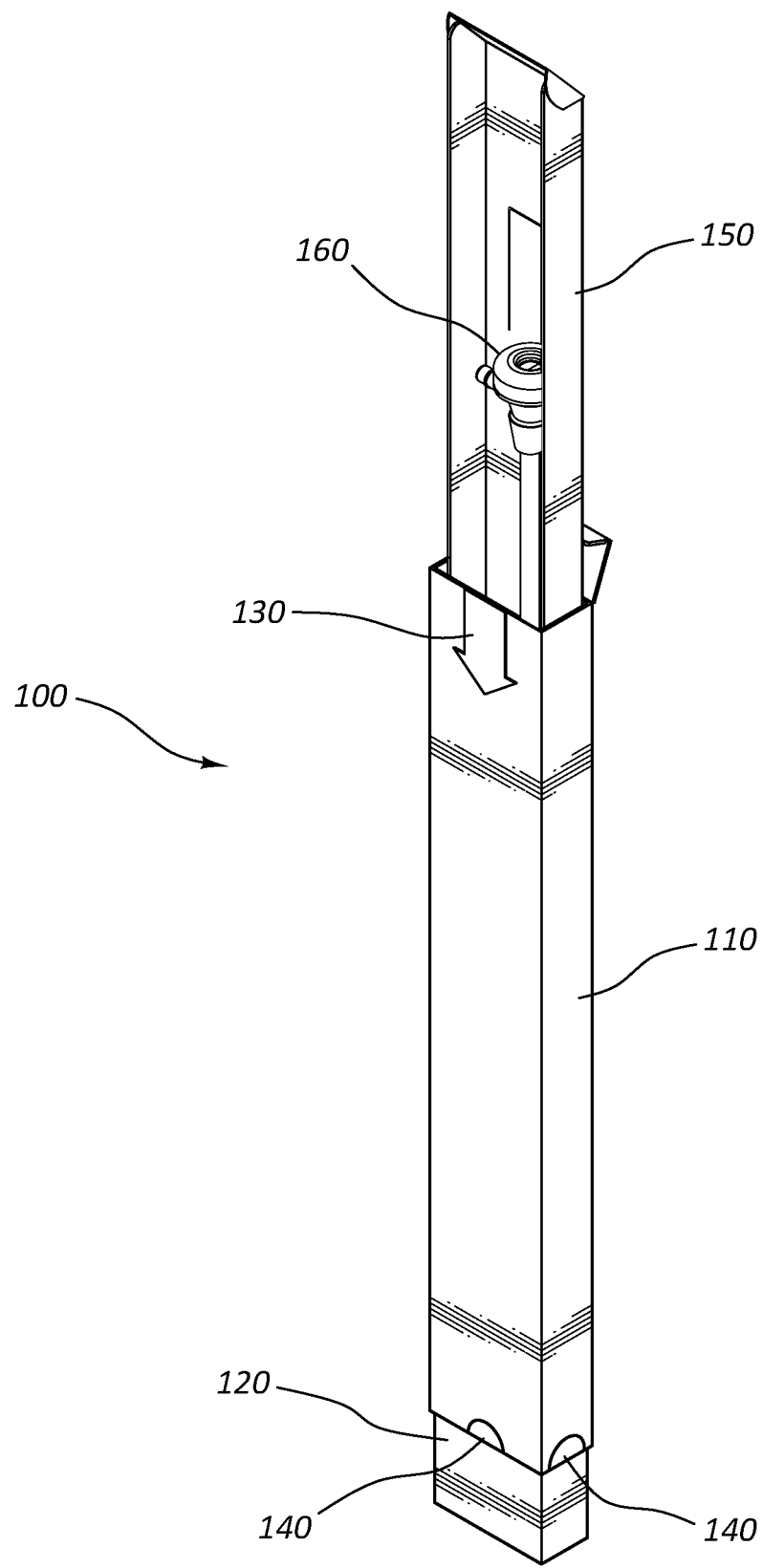
FIG. 2 is a perspective view of the packaging system of FIG. 1 in an open configuration.
Figure 3:
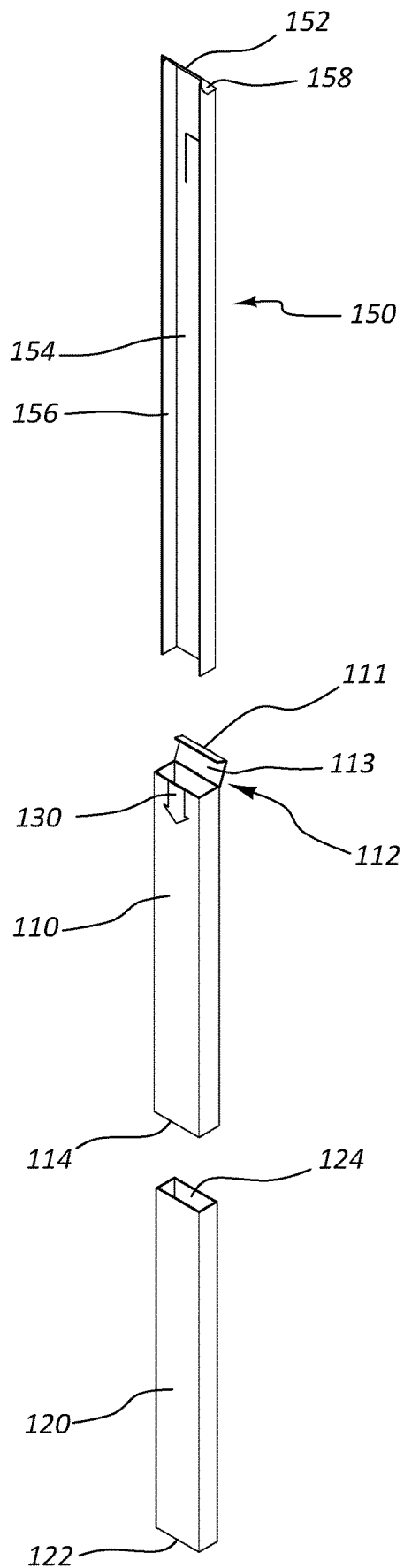
FIG. 3 depicts an exploded view of the packaging system of FIG. 1.

FIGS. 1-3 depict an embodiment of a packaging system 100 for a medical device. FIG. 1 depicts a perspective view of packaging system 100 for the medical device in a closed configuration. In the closed configuration, the user is unable to access the medical device within packaging system 100. FIG. 2 depicts a perspective view of packaging system 100 in an open configuration. In the open configuration, the user is able to access and remove the medical device. FIG. 3 depicts an exploded view of packaging system 100 and its various components.

Packaging system 100 may include an outer sleeve or box 110, an inner sleeve or box 120, a closure seal 130, and a plurality of coupling elements 140 to couple outer sleeve 110 to inner sleeve 120. Outer sleeve 110 and inner sleeve 120 may be adjustable telescoping boxes that have corresponding shapes that enable outer sleeve 110 and inner sleeve 120 to move relative to each other, inner sleeve 120 being slightly smaller than outer sleeve 110 to enable outer sleeve 110 to slide over inner sleeve 120. Outer sleeve 100 and inner sleeve 120 may be the same length or different lengths. FIG. 1 depicts the cross-section of outer sleeve 110 and inner sleeve 120 as rectangular; however, the present disclosure is not so limited. The cross-sections of outer sleeve 110 and inner sleeve 120 may be square, circular, triangular, polygonal, etc.

Outer sleeve 110 may include an open end 114 and a closure flap 112 for closing an end opposite open end 114. Closure flap 112 helps prevent dust and contaminants from entering packaging system 100 after the medical device has been placed within packaging system 100. Closure flap 112 may be hinged to outer sleeve 110 and closure flap 112 may have a free end 111. Inner sleeve 120 may have a similar configuration with an open end 124 and a closure flap 122 to close an end opposite open end 124.

Open end 114 of outer sleeve 110 slides over inner sleeve 120 and enables the outer sleeve 110 and the inner sleeve 120 to slide relative to each other. FIG. 1 depicts packaging system 100 in the closed configuration in which outer sleeve 110 overlaps inner sleeve a first distance. FIG. 2 depicts packaging system 100 in an open configuration in which outer sleeve 110 has been displaced over inner sleeve 120 to reveal a medical device 160 within packaging system 100. In the open configuration, outer sleeve 110 overlaps inner sleeve 120 a second distance, which is greater than the first distance but less than or equal to the length of inner sleeve 120.

Since the outer sleeve 110 and the inner sleeve 120 are adjustable relative to each other, the manufacturer may adjust the overall length of packaging system 100 by sliding outer sleeve 110 relative to inner sleeve 120 to fit a variety of different medical devices within packaging system 100. Because packaging system 100 is adjustable to the size of medical device 160, the manufacturer does not have to keep a large assortment of different size boxes.

After medical device 160 is stored within packaging system 100, the manufacturer may close the opening of outer sleeve 110 with closure flap 112. For example, FIG. 1 depicts packaging system 100 in the closed configuration. To help ensure that closure flap 112 remains closed during transportation, free end 111 of closure flap 112 may be coupled to outer sleeve 110 by closure seal 130. Closure seal 130 couples outer sleeve 110 and closure flap 112 together along an edge 116 between closure flap 112 and outer sleeve 110. The term "seal" does not imply that closure seal 130 "seals" packaging system 100 to be air-tight or prevent leakage, etc., but merely implies that packaging system 100 is closed. Closure seal 130 may be a sticker, decal, or label, with an adhesive to attach or couple closure flap 112 and outer sleeve 110.

Closure seal 130 may include a frangible seam 132 that extends from a first end 134 of closure seal 130 to a second end 136 of closure seal 130 along edge 116. Frangible seam 132 may be a weakened, brittle, or perforated portion of closure seal 130 that helps the user open closure flap 112. For example, if a force is applied to an inner surface 113 of closure flap 112, frangible seam 132 breaks to enable closure flap 112 to open outward. Frangible seam 132 may be a perforated seam with a plurality of holes that correspond with edge 116.

Packaging system 100 may further include a plurality of coupling elements 140. Coupling elements 140 may be stickers, decals, and labels, with an adhesive portion that couples outer sleeve 110 to inner sleeve 120. After medical device 160 is placed within packaging system 100, the overall length of packaging system 100 may be adjusted by sliding outer sleeve 110 over inner sleeve 120 until medical device 160 fits snugly within packaging system 100. The outer sleeve 110 and the inner sleeve 120 may be coupled together by placing coupling elements 140 at a location that adheres to both outer sleeve 110 and inner sleeve 120 (e.g., where open end 114 meets inner sleeve 120). Coupling elements 140 secure outer sleeve 110 to inner sleeve 120 and help maintain the overall length of packaging system 100. Coupling elements 140 couple outer sleeve 110 to inner sleeve 120 until a predetermined amount of compression force is applied to coupling elements 140. When the predetermined amount of compression force is applied, coupling elements 140 may peel away from inner sleeve 120 and curl under outer sleeve 110. When coupling elements 140 peel away from inner sleeve 120, outer sleeve 110 may slide with respect to inner sleeve 120 in a longitudinal direction of packaging system 100.

Packaging system 100 may further include a stiffener 150 to strengthen the overall packaging system 100. Stiffener 150 may include a leading edge 152, a base 154, a pair of side walls 156 that are orthogonal to base 154, and a pair of flaps 158 attached to leading edge 152 that interact with the top of side walls 156. The length of stiffener 150 is greater than outer sleeve 110 and inner sleeve 120, but less than the combined length of outer sleeve 110 and inner sleeve 120. When stiffener 150 is within packaging system 100, flaps 158 are constrained by side walls 156 and the inner surface of outer sleeve 110. Medical device 160 may be disposed in base 154 of stiffener 150. In some embodiments, a tray houses medical device 160 and the tray is disposed within base 154 of stiffener 150. In some embodiments, stiffener 150 may be the tray that houses medical device 160.

Stiffener 150 may provide additional support to packaging system 100 to increase the stiffness of packaging system 100. Packaging systems 100 that are long and have narrow cross-sections may need additional support to the center portion of packaging system 100 to protect medical device 160 within packaging system 100. Stiffener 150 may be more rigid, or stiffer, than outer sleeve 110 and/or inner sleeve 120. Stiffener 150 may be configured to increase various structural properties of packing system 100, by adding rigidity, stiffness, and so forth. Stiffener 150 may be fabricated from corrugated board, corrugated fiberboard, chipboard, plastics, and the like. Stiffener 150 may be configured to increase the compliance of packaging system 100 with the bridge impact test (ASTM D5265).

Figure 4:
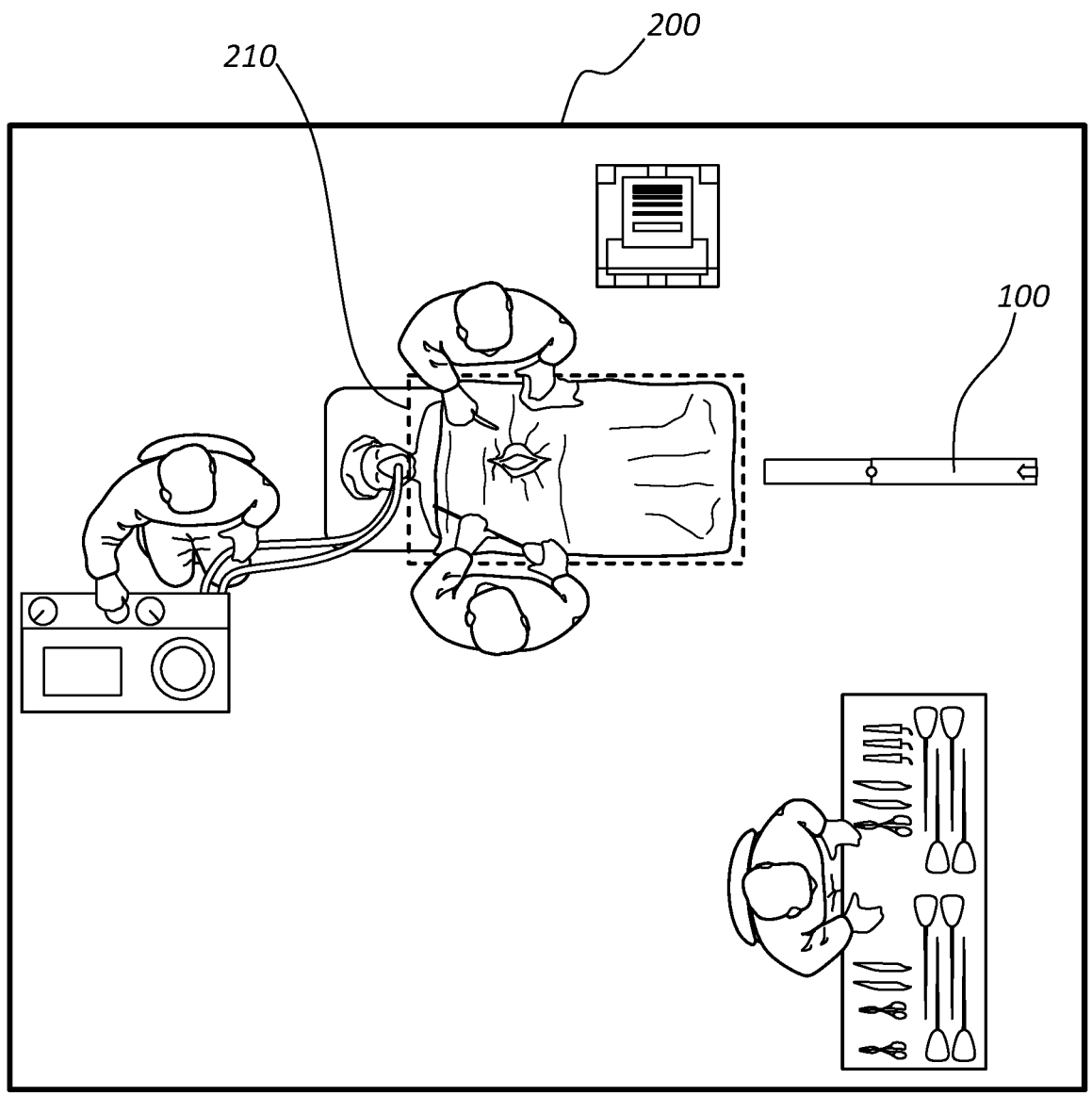
FIG. 4 depicts an operating room and a sterile field within the operating room.

FIG. 4 depicts an operating room 200 in which packaging system 100 may be used. A medical team creates a sterile field 210, a microorganism-free and spore-free area, within operating room 200 to perform a medical procedure on a patient. Sterile field 210 is created and maintained through the use of sterile gloves, gowns, drapes, etc., to create a barrier between the environment (including the members of the medical team) and the patient. Sterile field 210 helps prevent the spread of microorganisms or spores to the patient during the procedure.

Operating rooms may have limited space and must encompass all the personnel and equipment needed to perform a variety of different medical procedures. As discussed previously, medical devices that are long or oddly shaped may be difficult to access within operating room 200 due to space constraints; this may make it difficult to introduce medical device 160 into sterile field 210. For example, medical device 160 may be a central venous obstruction stent delivery apparatus that is over five feet in length. The central venous obstruction stent delivery apparatus needs to be stored in the original length as the catheter of the central obstruction stent delivery apparatus cannot be coiled as coiling the catheter may cause a kink (e.g., a sharp twist or curve) that would present complications during the medical procedure. Thus the five-foot-plus central venous obstruction stent delivery apparatus must be stored in a box that is five plus feet in length. In order to remove the central venous obstruction stent delivery apparatus, there would need to be 10 plus feet (e.g., the length of the device and the length of the package) to remove the device from the package. Accordingly, a method of opening packaging system 100 that would decrease the overall length to remove the device from packaging system 100 would be beneficial. Alternatively, packaging system 100 may be removed in a storage area before being introduced into the operating room.

Figure 5:
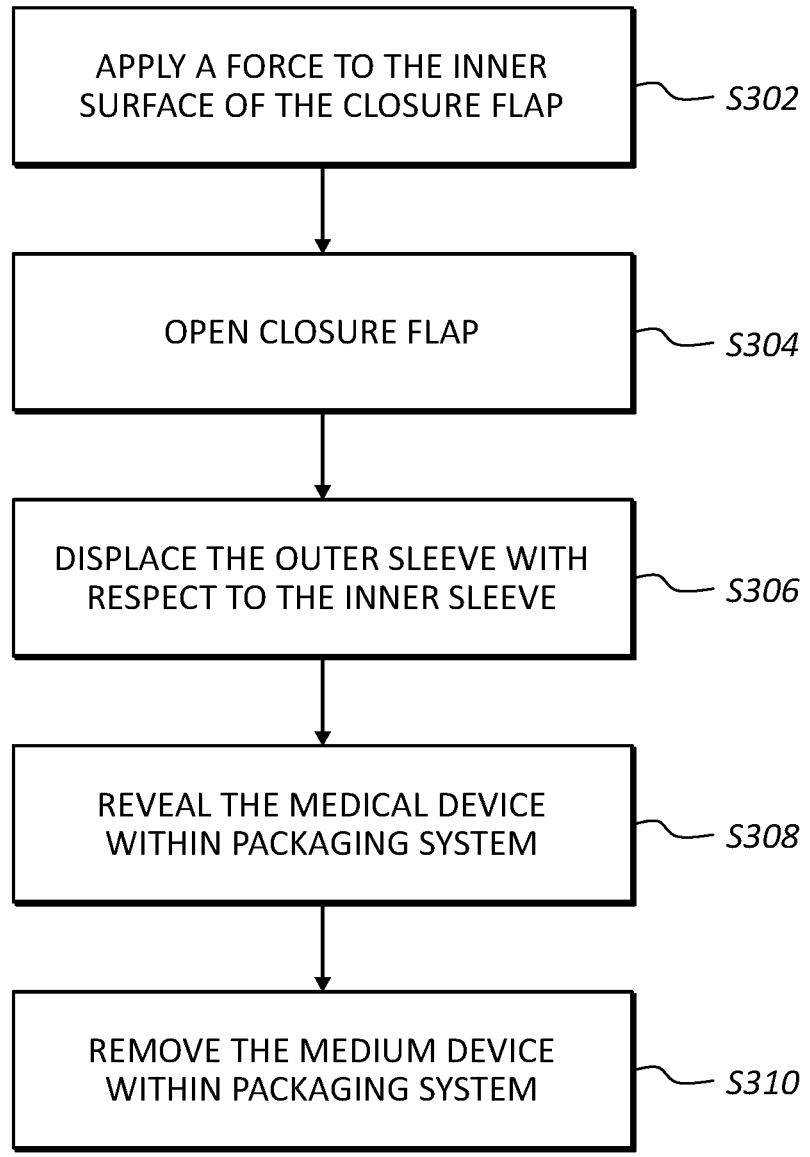
FIG. 5 depicts a flowchart of a method for opening the packaging system.

Stiffener 150 may be used to open packaging system 100 by applying a force to inside surface 113 of closure flap 112. FIG. 5 depicts a flowchart of a method for opening packaging system 100 in a manner that decreases the overall length needed to remove medical device 160 from packaging system 100. FIGS. 6-8 depict detailed views of how closure flap 112, stiffener 150, and outer sleeve 110 interact to open packaging system 100.

FIG. 6 depicts a detailed view of an upper portion of packaging system 100, specifically, outer sleeve 110, closure flap 112, closure seal 130, frangible seam 132, and edge 116. In S302, packaging system 100 is opened by applying a force to inner surface 113 of closure flap 112. For example, stiffener 150 disposed within packaging system 100 may apply a force to inner surface 113 of closure flap 112. Leading edge 152 of stiffener 150 may be angled or ramped toward a specific location of inner surface 113 of closure flap 112. For example, leading edge 152 may be angled toward edge 116 in order to concentrate the force applied to the inner surface close to frangible seam 132 of closure seal 130.

Flaps 158 of leading edge 152 are constrained during this process by side walls 156 and the inner surface of outer sleeve 110. Flaps 158 help distribute the force of leading edge 152 along the length of leading edge 152. In addition, flaps 158 help prevent leading edge 152 from collapsing when leading edge 152 contacts inner surface 113 of closure flap 112.

The force may be initiated in a number of different manners. The user may apply a downward force to closure flap 122 of inner sleeve 120. For example, the user may slam the bottom surface (e.g., closure flap 122 of inner sleeve 120) of packaging system 100 against the floor to apply the force. This force is transferred to stiffener 150 and the force is applied to inner surface 113 of closure flap 112. The user may also apply a downward force to outer sleeve 110 to slide outer sleeve 110 toward inner sleeve 120. This movement would place inner surface 113 of closure flap 112 in contact with stiffener 150 and thus apply a force to inner surface 113 of closure flap 112. Alternatively, a combination of these forces may be applied to coincide with each other to apply the force to the inner surface of closure flap 112, such as the user slamming packaging system 100 against the floor while simultaneously pulling outer sleeve 110 toward inner sleeve 120.

In S304, closure flap 112 is opened by breaking closure seal 130. Closure seal 130 couples free end 111 of closure flap 112 to outer sleeve 110 and includes frangible seam 132 along edge 116. Stiffener 150 applies a force directed toward frangible seam 132 of closure seal 130 to break closure seal 130. A predetermined amount of force breaks frangible seam 132 and opens closure flap 112 outward, as depicted in FIG. 7.

In S306, the user displaces outer sleeve 110 with respect to inner sleeve 120 and slides outer sleeve 110 toward inner sleeve 120 and inner sleeve 120 remains in a fixed position. As discussed above, if the user slams the bottom surface of packaging system 100 against the floor, the inner sleeve 120 remains in a fixed position. As the user slides outer sleeve 110 toward inner sleeve 120, stiffener 150 projects out of the opening of outer sleeve 110 as depicted in FIG. 8. Coupling elements 140 peel away from inner sleeve 120 and curl up inside outer sleeve 110, as depicted in FIG. 2, as the user slides outer sleeve 110 toward inner sleeve 120.

In S308, medical device 160 is revealed as the user continues to slide outer sleeve 110 toward inner sleeve 120. The user may continue to slide outer sleeve 110 either until outer sleeve 110 encounters the floor or until a sufficient amount of medical device 160 is revealed. For example, at least one third of stiffener 150 is revealed.

In S310, the user removes medical device 160 from packaging system 100. If at least one third of stiffener 150 is revealed, the user may remove medical device 160 at an angle. With one third of stiffener 150 revealed, the overall length required to remove medical device 160 is decreased by one third. Accordingly, the user does not have to extend medical device 160 the overall length of packaging system 100. Accordingly, the user is able to easily access medical device 160 without cutting themselves with a sharp instrument, damaging medical device 160 or compromising the sterility of medical device 160.

Figure 9:
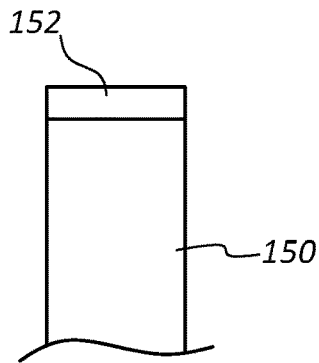
FIG. 9 depicts a detailed view of a stiffener of the packaging system of FIG. 2 with a flat leading edge.

FIGS. 9-13 depict alternative embodiments of packaging system 100. FIG. 9 depicts a front view of an embodiment of stiffener 150 with leading edge 152 that is straight or flat. A straight edge of leading edge 152 enables the entire leading edge 152 of stiffener 150 to contact inner surface 113 of closure flap 112 and disperse the force along the entire leading edge 152.

Figure 10:
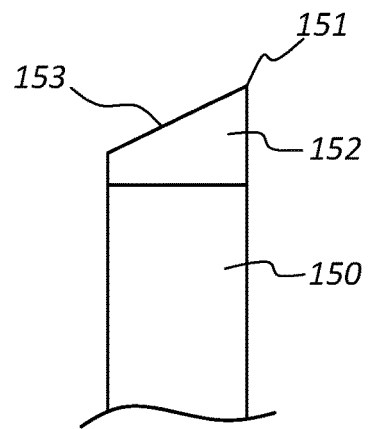
FIG. 10 depicts a detailed view of the stiffener with a tapered leading edge.

FIG. 10 depicts a front view of an embodiment of stiffener 150 in which leading edge 152 has a tapered edge 153. Tapered edge 153 terminates at a point 151 on one of the lateral edges of stiffener 150. In this embodiment, tapered edge 153 contacts inner surface 113 of closure flap 112 at a specific location and all of the force is applied to that location, rather than along the entire leading edge 152. Accordingly, frangible seam 132 may be broken in a specific manner. Alternatively, point 151 may be located at the center of leading edge 152 to contact frangible seam 132 or point 151 may be located at any other location along leading edge 152.

Figure 11:
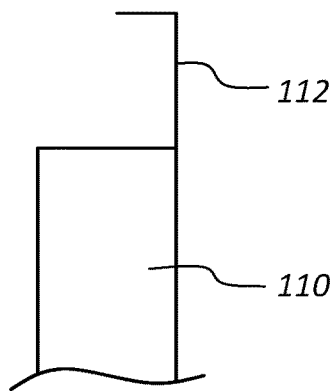
FIG. 11 depicts a detailed view of a closure flap of the packaging system of FIG. 1.

FIG. 11 depicts a side view of an embodiment of outer sleeve 110 and closure flap 112. Outer sleeve 110 does not include dust flaps and fold down from the side walls of outer sleeve 110 over the opening. In some embodiments, closure flap 112 may include dust flaps that fold down from the side walls of inner sleeve 120 to help cover the opening. Closure flap 122 may be the same or different than closure flap 112 and may include dust flaps that fold down from side walls 156 of inner sleeve 120.

Figure 12:
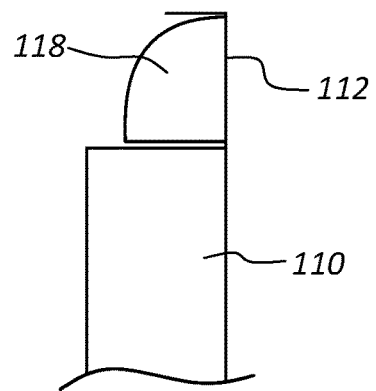
FIG. 12 depicts a detailed view of an embodiment of the closure flap with dust flaps.

FIG. 12 depicts a side view of an embodiment of outer sleeve 110 and closure flap 112 with a dust flap 118 that is coupled directly to closure flap 112. Only one dust flap 118 is depicted, however, a similar dust flap 118 may be coupled directed to the opposite end of closure flap 112. Dust flaps 118 help prevent dust and/or contaminants from entering packaging system 100. Additional types of dust flaps may be utilized to help prevent dust and/or contaminants from entering packaging system 100.

Figure 13:
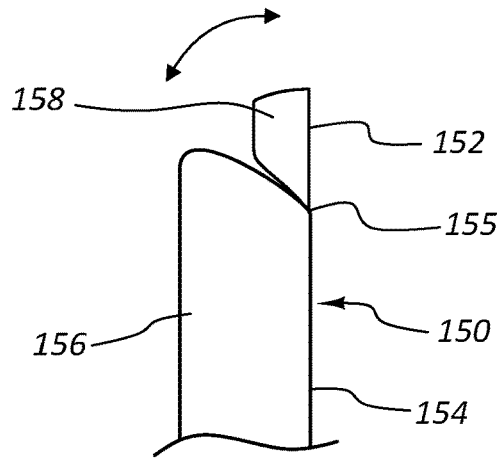
FIG. 13 depicts a detailed view of an embodiment of the stiffener illustrating how a first portion of the stiffener may rotate with respect to a second portion of the stiffener during use.

FIG. 13 depicts a side view of an embodiment of stiffener 150 and leading edge 152. Leading edge 152 may be attached to or hinged to base 154 of stiffener 150. In some embodiments, leading edge 152 or a first portion of stiffener 150 rotates with respect to base 154 or a second portion of stiffener 150 during use. Leading edge 152 may rotate about an axis of rotation 155 in the direction of the arrows. Accordingly, if leading edge 152 is upright when stiffener 150 begins to move toward inner surface 113 of closure flap 112, leading edge 152 will rotate toward side walls 156 and slide along inner edge 113 of closure flap 112 until leading edge 152 contacts side walls 156. Therefore, the angle of side walls 156 helps determine the location at which leading edge 152 encounters the inner surface of closure flap 112.

FIGS. 14 and 15 depict an embodiment of a packaging system 400 that resembles packaging system 100 described above in certain respects. Accordingly, like features are designated with like reference numerals, with the leading digits incremented to "4." For example, the embodiment depicted in FIGS. 14 and 15 include an outer sleeve 410 that may, in some respects, resemble the outer sleeve 110 of FIGS. 1-13. Relevant disclosure set forth above regarding similarly identified features thus may not be repeated hereafter. Moreover, specific features of packaging system 400 and related components shown in FIGS. 14 and 15 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the packaging system 400 and related components depicted in FIGS. 14 and 15. Any suitable combination of the features, and variations of the same, described with respect to the packaging system 100 and related components illustrated in FIGS. 1-13 can be employed with the packaging system 400 and related components of FIGS. 14 and 15, and vice versa. This pattern of disclosure applies equally to further embodiments depicted in subsequent figures and described hereafter, wherein the leading digits may be further incremented.

FIGS. 14 and 15 depict an embodiment of a packaging system 400 for a medical device. FIG. 14 depicts a detailed view of packaging system 400 for the medical device in a closed configuration. In the closed configuration, the user is unable to access the medical device within packaging system 400. FIG. 15 depicts a detailed view of packaging system 400 in an open configuration. In the open configuration, the user is able to access and remove the medical device.

FIGS. 14 and 15 depict a detailed view of an outer sleeve 410, a closure seal 430, and a locking tab 470 in a closed configuration and open configuration. Some embodiments may include dust flaps 418 as depicted in FIG. 15. Outer sleeve 410 includes a closure flap 412 for closing an opening (not shown in FIG. 14) of outer sleeve 410. Closure seal 430 may help ensure that closure flap 412 remains closed before the user wishes to access the medical device within packaging system 400. Closure seal 430 couples outer sleeve 410 and closure flap 412 together along an edge 416 between closure flap 412 and outer sleeve 410.

Locking tab 470 acts as an additional coupling feature to help secure closure flap 412 to outer sleeve 410. Locking tab 470 may be hinged to outer sleeve 410 a predetermined distance from edge 416. Locking tab 470 may further include a free end 472 that slides into a slot 474 of closure flap 412. As depicted in FIG. 15, slot 474 may be located on free end 411 of closure flap 412. When free end 472 of locking tab 470 is inserted into slot 474, locking tab helps secure closure flap 412 to outer sleeve 410. The user may unlock locking tab 470 by releasing or removing free end 472 from slot 474 and rotating locking tab 470 along the hinge away from outer sleeve 410.

Closure seal 430 may include frangible seams 432 and 434 that are located along edge 416 but do not cross into locking tab 470. Frangible seam 432 may be a weakened, brittle, or perforated portion of closure seal 430 that helps the user open closure flap 412. Once locking tab 470 is removed, the user may open packaging system 400 as previously discussed by applying a force to inner surface 413 of closure flap 412.

Another exemplary embodiment of a locking tab is illustrated in FIGS. 16 and 17. FIG. 16 depicts a detailed view of a packaging system 500 for a medical device in a closed configuration. In the closed configuration, the user is unable to access the medical device within packaging system 500. FIG. 17 depicts a detailed view of packaging system 500 in an open configuration. In the open configuration, the user is able to access and remove the medical device.

FIGS. 16 and 17 depict a detailed view of an outer sleeve 510, a closure seal 530, and a locking tab 570 in a closed configuration and open configuration. Some embodiments may include dust flaps 518 as depicted in FIG. 17. Outer sleeve 510 includes a closure flap 512 for closing an opening (not shown in FIG. 15) of outer sleeve 510. Closure seal 530 may help ensure that closure flap 512 remains closed before the user wishes to access the medical device within packaging system 500. Closure seal 530 couples outer sleeve 510 and closure flap 512 together along an edge 516 between closure flap 512 and outer sleeve 50.

Locking tab 570 acts as an additional coupling feature to help secure closure flap 512 to outer sleeve 510. Locking tab 570 may be hinged to outer sleeve 410 at edge 516. Locking tab 570 may further include a free end 572 that slides into a slot 574 of closure flap 512. As depicted in FIG. 15, slot 574 may be located on the top of closure flap 512. When free end 572 of locking tab 570 is inserted into slot 574, locking tab helps secure closure flap 512 to outer sleeve 510. The user may unlock locking tab 570 by releasing or removing free end 572 from slot 574 and rotating locking tab 570 along the hinge away from outer sleeve 510.

Closure seal 530 may include frangible seams 532 and 534 that are located along edge 516 but do not cross into locking tab 570. Frangible seam 532 may be a weakened, brittle, or perforated portion of closure seal 530 that helps the user open closure flap 512. Once locking tab 570 is removed or released, the user may open packaging system 500 as previously discussed by applying a force to inner surface 513 of closure flap 512.

With reference to the embodiments of FIGS. 14-17, as well as the other embodiments disclosed herein, packaging systems employing a frangible seal and no locking tab, a locking tab and no frangible seal, and both a locking tab and a frangible seal are within the scope of this disclosure. It is further within the scope of this disclosure to modify the embodiments above to including or remove the frangible seal and/or locking tab.

Figure 18:
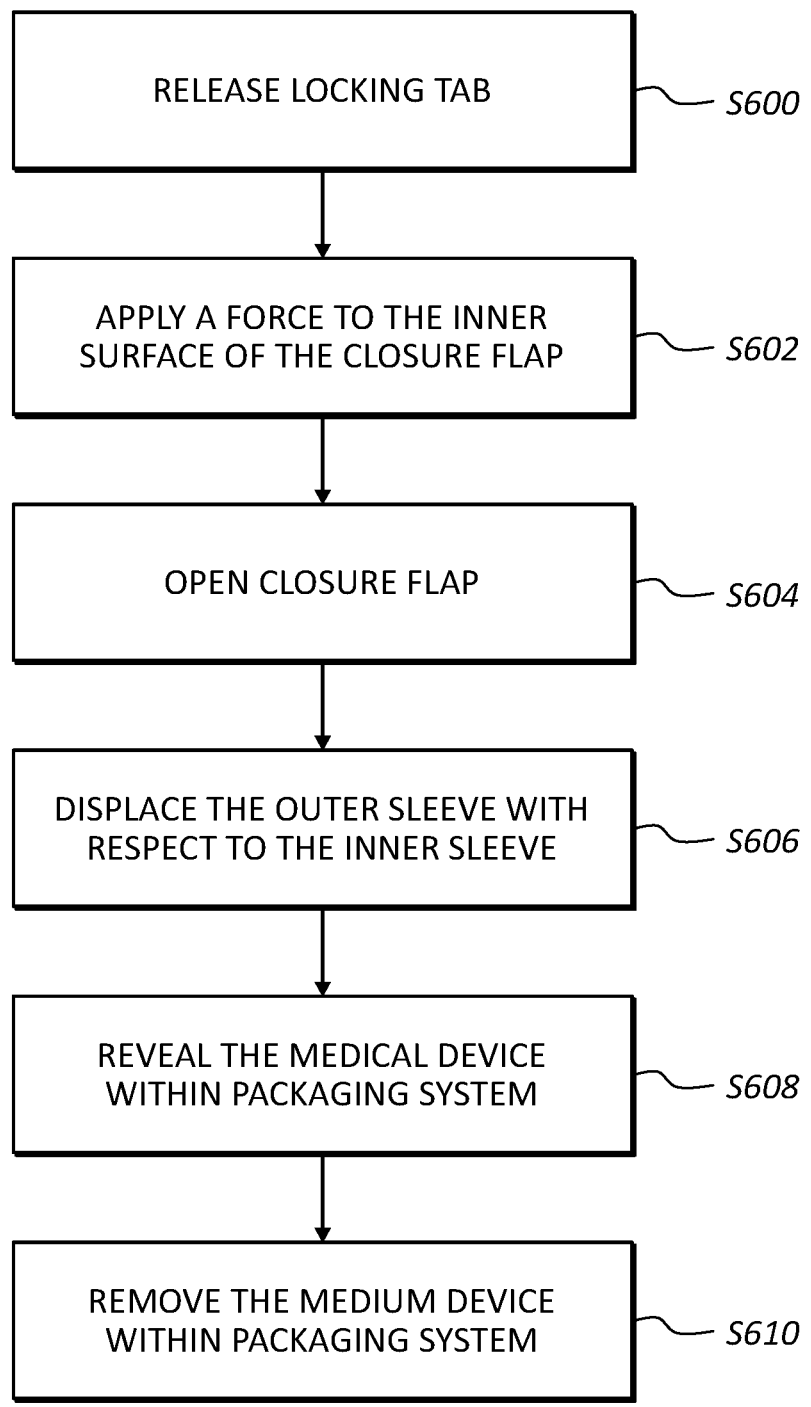
FIG. 18 depicts a flowchart of a method for opening the packaging systems of FIGS. 14 and 16.

FIG. 18 depicts a flowchart of a method for opening packaging systems 400 and 500 in a manner that decreases the overall length needed to remove medical device 160 from packaging systems 400 and 500. The flowchart of FIG. 18 is similar to the flowchart of FIG. 5 and relevant disclosure set forth above regarding similarly identified features (steps S602-S610) is not be repeated hereafter. In S600, the user releases locking tab 470 or 570 from closure flap 412 and 512. Once locking tab 470 and 570 are released from their respective slots 474 and 574, and the user may follow the remaining steps to open packaging system 400 and 500. Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A medical device packaging system, comprising:
   an outer sleeve with an open end and a closure flap for closing an end opposite the open end;
   a seal that couples the closure flap to the outer sleeve to close the end opposite the open end, wherein the seal is frangible along an edge between the closure flap and the outer sleeve;
   an inner sleeve with a corresponding shape to the outer sleeve, wherein the outer sleeve and the inner sleeve are configured to move relative to each other in a longitudinal direction of the inner and outer sleeves;
   a stiffener with a leading edge disposed within the inner and outer sleeves, the leading edge of the stiffener is configured to interact with an inner surface of the closure flap;
   a plurality of coupling elements that couple the outer sleeve to the inner sleeve, wherein the overall length of the medical device packaging system is greater than the length of the outer sleeve; and
   a medical device disposed within the stiffener.

2. The medical device packaging system of claim 1, wherein in a closed configuration, the plurality of coupling elements couple the outer sleeve to the inner sleeve, and
   wherein in an open configuration, the plurality of coupling elements are only attached to the outer sleeve.

3. The medical device packaging system of claim 1, wherein the leading edge of the stiffener is angled toward the frangible portion of the seal.

4. The medical device packaging system of claim 1, wherein the stiffener includes a base and a pair of side walls that are orthogonal to the base,
   wherein the leading edge is hinged to the base, and
   wherein the leading edge has a pair of flaps, each flap constrained by a side wall of the stiffener and an inner surface of the outer sleeve.

5. The medical device packaging system of claim 1, wherein the length of the stiffener is greater than the length of the outer sleeve.

6. The medical device packaging system of claim 1, wherein the leading edge of the stiffener is flat.

7. The medical device packaging system of claim 1, wherein the inner sleeve and the outer sleeve are telescoping boxes.

8. The medical device packaging system of claim 1, wherein the overall length of the packaging system is greater than five feet.

* * * * *